United States Patent
Badalamente et al.

(10) Patent No.: US 10,071,143 B1
(45) Date of Patent: Sep. 11, 2018

(54) METHODS FOR NON-SURGICAL TREATMENT OF CARPAL TUNNEL SYNDROME

(71) Applicant: The Research Foundation for The State University of New York, Albany, NY (US)

(72) Inventors: Marie A. Badalamente, Mount Sinai, NY (US); Edward Wang, Poquott, NY (US)

(73) Assignee: The Research Foundation for The State University of New York, Albany, NY (US)

( * ) Notice: Subject to any disclaimer, the term of this patent is extended or adjusted under 35 U.S.C. 154(b) by 0 days.

(21) Appl. No.: 14/988,205

(22) Filed: Jan. 5, 2016

Related U.S. Application Data

(63) Continuation-in-part of application No. 14/170,039, filed on Jan. 31, 2014, now abandoned, which is a continuation-in-part of application No. 13/688,387, filed on Nov. 29, 2012, now abandoned, which is a continuation of application No. 12/266,090, filed on Nov. 6, 2008, now Pat. No. 8,326,643, said application No. 14/170,039 is a continuation-in-part of application No. 12/730,688, filed on Mar. 24, 2010, now abandoned, which is a continuation-in-part of application No. 12/722,337, filed on Mar. 11, 2010, now abandoned, which is a continuation-in-part of application No. 12/266,090, filed on Nov. 6, 2008, now Pat. No. 8,323,643, and a continuation-in-part of application No. 12/115,256, filed on May 5, 2008, now Pat. No. 7,854,929, application No. 14/988,205, which is a continuation-in-part of application No. 12/722,337, filed on Mar. 11, 2010, now abandoned.

(60) Provisional application No. 60/927,437, filed on May 3, 2007.

(51) Int. Cl.
  *A61K 38/00* (2006.01)
  *A61K 38/48* (2006.01)
  *A61K 9/00* (2006.01)
  *A61K 35/74* (2015.01)

(52) U.S. Cl.
  CPC ........ *A61K 38/4886* (2013.01); *A61K 9/0019* (2013.01); *A61K 35/74* (2013.01); *C12Y 304/24003* (2013.01)

(58) Field of Classification Search
  None
  See application file for complete search history.

(56) References Cited

U.S. PATENT DOCUMENTS

| | | |
|---|---|---|
| 3,267,006 A | 4/1962 | Hakim et al. |
| 3,705,083 A | 12/1972 | Chiulli et al. |
| 4,174,389 A | 11/1979 | Cope |
| 4,338,300 A | 7/1982 | Gelbard |
| 4,524,065 A | 6/1985 | Pinnell |
| 4,645,668 A | 2/1987 | Pinnell |
| 5,173,295 A | 12/1992 | Wehling |
| 5,279,825 A | 1/1994 | Wehling |
| 5,332,503 A | 7/1994 | Lee et al. |
| 5,393,792 A | 2/1995 | Stern et al. |
| 5,422,103 A | 6/1995 | Stern et al. |
| 5,514,370 A | 5/1996 | Stern et al. |
| 5,589,171 A | 12/1996 | Wegman |
| 5,753,485 A | 5/1998 | Dwulet et al. |
| 5,830,741 A | 11/1998 | Dwulet et al. |
| 5,952,215 A | 9/1999 | Dwulet et al. |
| 5,989,888 A | 11/1999 | Dwulet et al. |
| 6,022,539 A | 2/2000 | Wegman |
| 6,060,474 A | 5/2000 | Williams et al. |
| 6,086,872 A | 7/2000 | Wegman |
| 6,086,877 A | 7/2000 | Nishioka et al. |
| 6,280,993 B1 | 8/2001 | Yamato et al. |
| 6,335,388 B1 | 1/2002 | Fotinos |
| 6,358,539 B1 | 3/2002 | Murad |
| 6,958,150 B2 | 10/2005 | Wegman et al. |
| RE39,941 E | 12/2007 | Wegman |
| 7,425,326 B2 | 9/2008 | Strauss |
| 7,854,929 B2 | 12/2010 | Badalamente et al. |
| 2003/0129178 A1 | 7/2003 | Wegman et al. |
| 2004/0137596 A1 | 7/2004 | Kurfurst et al. |
| 2006/0204488 A1 | 9/2006 | Badalamente |
| 2007/0224183 A1 | 9/2007 | Sabatino et al. |
| 2007/0224184 A1 | 9/2007 | Badalamente et al. |
| 2008/0009736 A1* | 1/2008 | Amadio ............... A61B 5/1107 600/453 |

(Continued)

FOREIGN PATENT DOCUMENTS

| | | |
|---|---|---|
| EP | 0677586 | 10/1995 |
| EP | 1433845 | 6/2004 |

(Continued)

OTHER PUBLICATIONS

Childs et al. (Circulation, vol. 102, 2000, 2391-2395).*
Patel et al. (AAOS Now, Jan. 2015, pp. 1-16).*
Jeyapalan et al. (Skeletal Radiol., vol. 38, pp. 1099-1103).*
Sawyer, Jeffrey R. et al., A reciprocal t(4;9)(q31;p22) in a solitary neurofibroma, Cancer Genetics and Cytogenetics 156 (2005) 172-174, Copyright 2005 Elsevier Inc.
Auxilium Pharmaceuticals Inc. (AUXL) DEF 14A Definitive proxy statements, Filed on Apr. 27, 2012, Filed Period Jun. 21, 2012, Thomson Reuters Accelus, pp. 90.

(Continued)

*Primary Examiner* — Hope Robinson
(74) *Attorney, Agent, or Firm* — Fox Rothschild LLP

(57) ABSTRACT

Provided is a non-surgical method of treatment of carpal tunnel syndrome by administering an effective amount of purified collagenase I and II by injection onto a transverse carpal ligament, without penetrating the transverse carpal ligament. The purified collagenase I and II are obtained from *Clostridium histolyticum*, and the effective amount is a dose comprising a concentration of approximately 0.29 mg of the purified collagenase I and II to one ml diluent.

11 Claims, No Drawings

(56) References Cited

U.S. PATENT DOCUMENTS

2010/0247513 A1  9/2010  Agee et al.
2013/0287759 A1  10/2013  Munoz Montano

FOREIGN PATENT DOCUMENTS

| JP | 2003523319 | 8/2003 |
|---|---|---|
| WO | WO 01/21574 | 3/2001 |
| WO | WO 2007/089851 | 8/2007 |

OTHER PUBLICATIONS

Angehrn, Fiorenzo et al., Can cellulite be treated with low-energy . . . , Clinical Investigations in Aging 2007:2(4) 623-630, Copyright 2007 Dove Medical Press Limited.

Welton, RL et al., Collagenase production by Achromobacter iophagus, Biochim Biophys Acta. Mar. 28, 1975;384(1):228-34, Abstract.

Badalamente, Marie A. et al., Enzymatic Capsulotomy for Adhesive Capsulitis (Frozen Shoulder) . . . , 61st Annual Am. Society for Surgery of the Hand, Sep. 2006, pp. 2.

Hannafin, Jo A. et al., Adhesive Capsulitis a Treatment Approach, Clinical Orthopaedics and Related Research, No. 372, 2000, pp. 95-109.

Siegel, Lori B. et al., Adhesive Capsulitis: A Sticky Issue, American Family Physician, The American Academy of Family Physicians, Apr. 1, 1999, pp. 12.

Hulstyn, Michael J. et al., Adhesive Capsulitis of the Shoulder, Orthopaedic Review, Apr. 1993, pp. 425-433.

Bond, Michael D., et al., Characterization of the Individual Collagenases from Clostridium histolyticum, Biochemistry, vol. 23, No. 13, 1984, pp. 3085-3091.

Hosaka, T. et al., Class2 collagenase, GenBank: BAA86030.1, http://www.ncbi.nlm.nih.gov/protein/BAA86030.1, Published Only in Database (1999), Submitted (Apr. 30, 1999), pp. 2.

Chen, Hong-Rong et al., Clinicopathological Study on Submucosal Injection of Collagenase in the Treatment of Submucous Fibrosis . . . , Kaohsiung J. Med. Sci. 2: 212-219, 1986.

Badalamente, Marie A. et al., Collagen as a Clinical Target: Nonoperative Treatment of Dupuytren's . . . , The Journal of Hand Surgery, vol. 27A No. 5, Sep. 2002, pp. 788-798.

Worthington Enzyme Manual, Copyright 2012—Worthington Biochemical Corporation, pp. 4.

Kilian, O. et al., The frozen shoulder. Athroscopy, histological findings and transmission electron microscopy imaging, Chirurg, 2001, 72, pp. 1303-1308.

De-Wever, Ivo et al., Cytogenetic, Clinical, and Morphologic Correlations . . . , Copyright 2000 the U.S. and Canadian Academy of Pathology, Inc., vol. 13, No. 10, pp. 1080-1085.

Hutchinson, J. W. et al., Dupuytren's disease and frozen shoulder induced . . . , The Journal of Bone & Joint Surgery (Br), vol. 80-B, No. 5, Sep. 1998, pp. 907-908.

Badalamente, Marie A. et al., Efficacy and Safety of Injectable Mixed Collagenase Subtypes in . . . , The Journal of Hand Surgery, vol. 32A No. 6 Jul.-Aug. 2007, pp. 767-774.

Badalamente M.A. et al: "Enzyme injection as a nonoperative treatment for Dupuytren's disease", Drug Delivery, vol. 3, 1996, pp. 35-40, XP000993396.

Ippolito, E. et al., Experimental study on the use of collagenase in localized connective tissue . . . , Ital. J. Orthop. Traumotol., (1975) vol. 1, No. 2, pp. 279-290, Abstract.

Bunker, T. D., Frozen shoulder: unravelling the enigma, Ann R Coll Surg Engl 1997; 79, pp. 210-213.

Yamato, I., et al., Gene encoding class I collagenase, GenBank: AAE80094.1, http://www.ncbi.nlm.nih.gov/protein/AAE80094, Patent: U.S. Pat. No. 6,280,993-A 3 Aug. 28, 2001, pp. 2.

WebMD Health News, Goodbye, Cellulite Thighs?, Copyright 2005-2007 WebMD, Inc., pp. 2.

Jung, Chang-Min et al., Identification of Metal . . . , Journal of Bacteriology, vol. 181, No. 9, May 1999, p. 2816-2822, Copyright 1999, American Society for Microbiology.

Oppenheim, F. et al., A modified procedure for the purification of clostridial collagenase, Prep Biochem. 1978;8(5):387-407, Abstract.

Galardy, Richard E. et al., Inhibition of Collagenase from Clostridium histolyticum by Phosphoric and Phosphonic Amides, Biochemistry, vol. 22, No. 19, 1983, pp. 4456-4561.

Hurst, Lawrence C. et al., Injectable Clostridial Collagenase: Striving Toward Non . . . , available at http://www.aos.org/research/committee/research/KAPPA/KD2009_Hurst.pdf.

Rotunda, Adam M. et al., Mesotherapy and Phosphatidylcholine Injections: Historical . . . , Copyright 2006 by the American Society for Dermatologic Surgery, Inc., pp. 465-480.

Dimarcantonio, Tina, Multiple collagenase injections effective, safe for treating 'frozen shoulder', www.ORTHOSuperSite.com, May 16, 2006, pp. 2.

Mandl, Ines et al., Multiplicity of Clostridium histolyticum Collagenases, Multiplicity of Collagenases, vol. 3, No. 11, Nov. 1964, pp. 1737-1741.

Ochs, Ridgely, Personal Health/Promising New Treatments for Stiff-Shoulder Condition, www.Newsday.com, Oct. 1, 2001, pp. 3.

Bains, M. et al., Journal of Bone and Joint Surgery, Primary Frozen Shoulder, The Untold Story!, British Volume, vol. 90-B, Issue SUPP_II, 352, (Abstract) 2008, pp. 2.

Park, Pyo-Jam et al., Purification and Characterization of a Collagenase from the . . . , Journal of Biochemistry and Molecular Biology, vol. 35, No. 6, Nov. 2002, pp. 576-582.

Sugasawara, R. et al., Purification and characterization of three forms of collagenase from Clostridium histolyticum, Biochemistry Oct. 23, 1984;23(22):5175-81, Abstract.

Nagano, Hiroko et al., Purification of Collagenase and Specificity of Its Related Enzyme from Bacillus subtilis FS-2, Biosci. Biotechnol. Biochem., 63 (7) 1999, pp. 181-183.

Ambrosius, D.D. et al., Recombinant collagenase type II from clostridium . . . , GenBank:CAA02888.1, http://www.ncbi.nlm.nih.gov/proteinCAA02888, Patent: EP0677586-A1, Oct. 18, 1995.

Jin, Bo et al., Reversibility of experimental rabbit liver cirrhosis by portal collagenase administration, Laboratory Investigation (2005) 85, 992-1002, 2005 USCAP, Inc.

Netti, Paolo A. et al., Role of Extracellular Matrix . . . , ICancer Research 60. 2497-2503. May 1, 20001, Copyright 2000 American Association for Cancer Research, pp. 2497-2503.

Balci, N. et al., Shoulder adhesive capsulitis and shoulder range of motion in type II diabetes mellitus . . . , Journal of Diabetes, May-Jun. 1999(3): 135-40 (Abstract).

Keil, B., Some newly characterized collagenases from procaryotes and lower eucaryotes, Mol Cell Biochem. Jan. 26, 1979;23(2) 87-108, Abstract.

Griffith, James F. et al., Sonography of Plantar Fibromatosis, AJR:179, Nov. 2002, pp. 1167-1172.

Stony Brook Announces New Clinical Trial with BioSpecifics' Injectable Collagenase for Adhesive Capsulitis, http://web.archive.org/web/20011020004505/, May 8, 2012, (pp. 2).

Matsushita, Osamu et al., Substrate Recognition by the Collagen-binding Domain . . . , The Journal of Biological Chemistry, vol. 276, No. 12, Issue of Mar. 23, pp. 8761-8700, 2001.

Successful phase II results lead to phase III approval—Dupuytren disease, obgyn.net Headline News, Oct. 8, 2001 (Oct. 8, 2011), XP008125855.

Evans, Christopher H., The lanthanide-enhanced affinity chromatography of clostridial collagenase, Biochem. J. (1985) 225, 553-556.

Bunker, T. D. et al, The Pathology of Frozen Shoulder a Dupuytren-Like Disease, The Journal of Bone and Joint Surgery, vol. 77-B, No. 5, Sep. 1995, pp. 677-683.

Atroshi, Isam et al., Prevalence of Carpal Tunnel Syndrome in a General Population, JAMA, Jul. 14, 1999—vol. 281, No. 2, Copyright American Medical Association, pp. 153-158.

Graham, Brent et al., Development and Validation of Diagnostic Criteria for Carpal Tunnel Syndrome, The Journal of Hand Surgery, vol. 31A No. 6 Jul.-Aug. 2006, pp. 6.

(56) References Cited

OTHER PUBLICATIONS

Gaughan et al. (Am. J. Vet. Res., vol. 52, No. 5, May 1991).
Krane (J. Invest. Dermat. vol. 79, pp. 83s-86s, 1982).
Crane (J. Invest. Dermatol., Jul. 1982, vol. 79, Supp.1, pp. 83s-86s).
Desouza et al. (FASEB J., vol. 10, pp. 927-930, 1996).
Shimizu et al. (The Anatomical Record, 1988, vol. 220, pp. 138-142).
Fusetti et al., (Am. J. Orthop. 2009, vol. 38 (4), pp. 181-186).
Paige et al. (Int'l. Biodeterior. & Biodegrad., vol. 50, pp. 1-10, 2002).
Wilson, J. K. et al., A review of treatment for carpal tunnel syndrome, Disability and Rehabilitation, 2003; vol. 25, No. 3, 113-119, Copyright 2003 Taylor & Francis Ltd.

* cited by examiner

METHODS FOR NON-SURGICAL TREATMENT OF CARPAL TUNNEL SYNDROME

PRIORITY

This application is a continuation in part of U.S. patent application Ser. No. 14/170,039, filed on Jan. 31, 2014, now abandoned, which is a continuation in part to U.S. patent application Ser. No. 13/688,387, now abandoned, filed Nov. 29, 2012 and U.S. patent application Ser. No. 12/730,688, filed Mar. 24, 2010, now abandoned. U.S. patent application Ser. No. 13/688,387 is a continuation of U.S. patent application Ser. No. 12/266,090, filed Nov. 6, 2008, now issued as U.S. Pat. No. 8,323,643. U.S. patent application Ser. No. 12/730,688 is a continuation in part of U.S. patent application Ser. No. 12/722,337, filed Mar. 11, 2010, which is a continuation in part of U.S. patent application Ser. No. 12/266,090, filed Nov. 6, 2008, now issued as U.S. Pat. No. 8,323,643 and U.S. patent application Ser. No. 12/115,256, filed May 5, 2008, now issued as U.S. Pat. No. 7,854,929, which claims priority to U.S. Provisional Patent Application No. 60/927,437, filed May 3, 2007. The present application is also a continuation in part of U.S. patent application Ser. No. 12/722,337, filed Mar. 11, 2010, which is a continuation in part of U.S. patent application Ser. No. 12/266,090, filed Nov. 6, 2008, and U.S. patent application Ser. No. 12/115,256, filed May 5, 2008, now issued as U.S. Pat. No. 7,854,929.

FEDERAL FUNDING

This invention was made with government support under Grant No. RR010710 awarded by the National Institutes of Health. The government has certain rights in the invention.

BACKGROUND OF THE INVENTION

The carpal tunnel is a space in the palm region of a human hand, with a floor of the carpal tunnel formed by a concave arch of carpal bones covered by wrist ligaments and a roof of the carpal tunnel formed by transverse carpal ligament extending in a transverse direction across the wrist from a base of the thumb to an outer portion of the wrist bones. The carpal tunnel forms a conduit for the median nerve and digital flexor tendons extending from the forearm into the palm.

Carpal tunnel syndrome is a condition where a reduction in the size of the carpal tunnel compresses the median nerve, resulting in pain and/or numbness in the wrist and/or hand. Compression of the median nerve can also result from an increase in the volume of the tissue inside the carpal tunnel or movement of the flexor tendons. Compression of the median nerve can cause pain, numbness or other adverse sensation in the wrist, hand, fingers or thumb that can radiate to the forearm.

Conventional methods to treat early stage carpal tunnel syndrome can include injection of non-steroidal anti-inflammatory drugs, splinting and/or injection of corticosteroid. Surgery to obtain carpal tunnel release is generally recommended after six to seven weeks of conservative treatments when persistent signs of aggravated two point discrimination and an electromyography results indicating diminished nerve conduction velocities.

Carpal tunnel release is a surgical procedure that is commonly performed in the field of hand surgery. Various surgical methods to obtain carpal tunnel release include open, limited incision and endoscopic techniques. Surgery for carpal tunnel release involves a simple incision of the transverse carpal ligament to relieve direct compression on the median nerve in the carpal tunnel. Such surgery seeks to minimize damage to the superficial palmar arch vessels, to avoid incision induced scars, and to avoid injury to nerves, e.g., the palmar cutaneous branch of the median nerve, thenar branch, or median, ulnar and digital nerves. VanDoesburg et al. describe pathologic findings in patients with carpal tunnel syndrome of non-inflammatory fibrosis and thickening of the subsynovial connective tissue, including the transverse carpal ligament. See, VanDoesburg M H, et al., *Sonographic Measurements Of Subsynovial Connective Tissue Thickness In Patients With Carpal Tunnel Syndrome*, J. Ultrasound Medicine 31:31-36 (2012).

SUMMARY OF THE INVENTION

The present disclosure has been made to address the above-mentioned problems and disadvantages, and to provide at least the advantages described below. Accordingly, an aspect of the present disclosure relates to the discovery that collagenase injections are effective to lyse collagenous adhesions in the carpal tunnel to treat the carpal tunnel syndrome. As such, the present disclosure provides a non-surgical method of treating carpal tunnel syndrome that includes administering an effective amount of purified collagenase I and II by injection onto a transverse carpal ligament of the patient, with the injection not penetrating the transverse carpal ligament, with the purified collagenase I and II being obtained from *Clostridium histolyticum*, and with the effective amount being a dose comprising a concentration of 0.29 mg or more of the purified collagenase I and II to one ml diluent.

DETAILED DESCRIPTION OF EMBODIMENTS OF THE PRESENT INVENTION

The present disclosure relates to the discovery that collagenase injections are effective to lyse collagenous adhesions in the carpal tunnel and treat carpal tunnel syndrome. As such, the disclosure relates to methods of treating or preventing carpal tunnel syndrome in a patient in need of such treatment includes injecting or otherwise delivering an effective amount of collagenase to the collagenous adhesions in the carpal tunnel. The disclosure also relates to the use of collagenase in the manufacture of a medicament to treat carpal tunnel. Collagenase injections have been proposed for the treatment of diseases such as Duptyren's disease and Peyronie's disease. Both diseases are associated with collagen plaques or cords. Wegman, Thomas L., U.S. Pat. No. 5,589,171, Dec. 31, 1996, U.S. Pat. No. 6,086,872, Jul. 11, 2000 and U.S. Pat. No. 6,022,539, Feb. 8, 2000. Collagenase is an enzyme that has the specific ability to digest collagen. A preferred form of collagenase is derived from fermentation by *Clostridium histolyticum*, and is purified by a chromatographic technique, as disclosed at U.S. Pub. No. 2007/0224183 A1 of Sabatino et al., issued as U.S. Pat. No. 7,811,560. Collagenase naturally produced by *Clostridium histolyticum* once purified will exhibit two distinct peaks when run on an electrophoresis SDS gel. These two distinct peaks are referred to as collagenase I and collagenase II.

Sterilized lyophilized collagenase powder is commercially available having a minimum assay of 50 ABC units per mg. The assay may range considerably above that from batch to batch, but is taken into account in determining the weight of powder to use with a pharmaceutically acceptable carrier, e.g. normal saline, in preparing a desired concentration for treatment.

A preferred collagenase composition includes a mixture of collagenase I and collagenase II in a mass ratio of about 1 to 1 and having specific activity of at least about 700 SRC units/mg, such as at least about 1,000 SRC units/mg, more preferably at least about 1500 SRC units/mg. One SRC unit will solubilize rat tail collagen into ninhydrin reaction material equivalent to 1 nanomole of leucine per minute, at 25° C., pH 7.4. Collagenase has been described in ABC units as well, with 10,000 ABC units equaling approximately 0.58 mg of collagenase. This potency assay of collagenase is based on the digestion of undenatured collagen (from bovine tendon) at a pH of 7.2 and 37 degrees C. for 20-24 hours. The number of peptide bonds cleaved is measured by reaction with ninhydrin. Amino groups released by a trypsin digestion control are subtracted. One net ABC unit of collagenase will solubilize ninhydrin reactive material equivalent to 1.09 nanomoles of leucine per minute. 1 SRC unit equal approximate 6.3 ABC units or 18.5 GPA units.

The collagenase is administered via injection in a pharmaceutically acceptable liquid carrier that does not interact or deactivate the collagenase. Examples are normal saline, aqueous NaCl/CaCl$_2$ buffer (e.g., containing 0.9% NaCl and 2 mM CaCl$_2$), aqueous dextran solution, and aqueous hetastarch solution. For example, the lyophilized formulation can contain 0.1 mg lactose monohydrate per 1,000 ABC units, with each glass vial containing 5,150 ABC units of enzyme.

In accordance with the present disclosure, collagenase in a liquid carrier is injected into a collagen adhesion within the carpal tunnel. The amount and concentration of collagenase used are effective to soften and relax or rupture the adhesion.

AA4500, i.e., collagenase *clostridium histolyticum*, is injected onto, not into, the transverse carpal ligament using ultrasound guidance, in the proximal carpal tunnel (wrist crease), mid carpal tunnel (hook of the hamate) and distal carpal tunnel (distal edge of the ligament), in patients, to lyse type 1 collagen. The AA4500 functions as an enzymatic scalpel to rupture the transverse carpal ligament.

The tunnel contains nine tendons and the median nerve. The thickness of the transverse carpal ligament is ascertained in the proximal, mid and distal carpal tunnel for each patient.

Using ultrasound guidance, an 18 gauge needle punctures the skin, without puncturing the transverse carpal ligament, in the proximal, mid and distal carpal tunnel, simulating a lidocaine injection, to provide needle tracks for subsequent AA4500 delivery.

Using ultrasound guidance, a blunt tipped needle (Sprotte) follows the needle tracks. The AA4500 is injected onto, without penetrating, the transverse carpal ligament of each hand of a patient, in the proximal, mid and distal tunnel in three equal aliquots of 0.29 mg AA4500/1 ml, with a concentration of 0.29 mg/ml. Alternative embodiments are 0.58 mg AA4500/1 ml, with a concentration of 0.58 mg/ml, 0.58 mg AA4500/2 ml, with a concentration of 0.29 mg/ml, and 0.58 mg AA4500/0.5 ml, with a concentration of 1.16 mg/ml.

The AA4500 is injected with 1 ml Endo dilution, with a dosing group (n=2) and a placebo group (n=4), with a placebo of 1 ml, for control since the placebo will not rupture the transverse carpal ligament.

Twenty-four hours are allowed to lapse following the injection, for collagen lysis of the transverse carpal ligament. After lapse of the twenty-four hours, each hand of the patient is placed, palmar surface down, on a table top. A gentle pressure applied to force the hand flat against the table top, and manipulation procedure is performed utilizing a specially designed instrument having a steel ball attached to a standard tip/pinch meter, to apply a force of pressure measured in kg or lbs. The transverse carpal ligament is aligned on the steel ball and pressure is applied from the dorsal side of the hand to at least 10 lbs.

Ultrasound imaging is performed at the proximal, mid and distal carpal tunnel to detect thickness of the transverse carpal tunnel or evidence that the ligament has been partially or completely ruptured by the AA4500.

The total volume of liquid injected is preferably 2.0 ml or less, with a smaller volume down to about 0.5 ml to about 0.1 ml being preferred.

The injection is preferably administered with an anesthesia injection of 5-10 ml sterile 1% lidocaine preferably preceding the collagenase injection for patient comfort.

The total dosage is preferably injected in one portion, although two or more portions at the same or different but adjacent points are possible, to assure good distribution of the collagenase within a small volume of the adhesion.

The patient can be any animal, preferably a mammal or human patient. Examples of animals that can be treated according to the present disclosure include domestic animals (such as cats, dogs, etc.), farm animals (such as horses, cows, pigs, etc.) and exotic animals (such as monkeys, apes, etc.). Preferred human patients are those that have decreased finger/carpal tunnel motion which occurred idiopathically, after trauma or patients with diabetes and/or thyroid disorders.

The patient is characterized as having pain that has increased to a level that interferes with activities of daily living and diminishes the quality of life. The present disclosure achieves improvement in all planes of motion.

Accordingly, a non-surgical method is provided for treatment of carpal tunnel syndrome that includes administering an effective amount of purified collagenase I and II by injection onto a transverse carpal ligament of the patient, with the injection not penetrating the transverse carpal ligament, with the purified collagenase I and II being obtained from *Clostridium histolyticum*, and with the effective amount being a dose comprising a concentration of 0.29 mg or more of the purified collagenase I and II to one ml diluent.

While the invention has been shown and described with reference to certain embodiments thereof, it will be understood by those skilled in the art that various changes in form and detail may be made therein without departing from the spirit and scope of the invention as defined by the appended claims, and equivalents thereof.

What is claimed is:

1. A non-surgical method of treating carpal tunnel syndrome in a subject in need thereof, the method comprising:
    administering by injection, an effective amount of purified collagenase onto a transverse carpal ligament of the subject, wherein the effective amount of the purified collagenase is at least 0.58 mg/ml with a specific activity of at least 1500 SRC units, wherein the purified collagenase is obtained from *Clostridium histolyticum* and comprises collagenase I and II, and wherein the collagenase is administered with a blunt needle.

2. The method of claim 1, wherein the collagenase is injected in a liquid pharmaceutically acceptable carrier.

3. The method of claim 1, wherein the effective amount of the purified collagenase is injected between three and six sites onto a palmar side of the transverse carpal ligament of the subject.

4. The method of claim 1, wherein the injection is onto the transverse carpal ligament, without penetrating the transverse carpal ligament.

5. The method of claim 1, wherein the injection is performed with ultrasound guidance to avoid penetration of the transverse carpal ligament.

6. The method of claim 1, wherein the purified collagenase functions to rupture the transverse carpal ligament.

7. The method of claim 1, wherein an anesthetic is injected prior to administration of the collagenase, and wherein the injection of the anesthetic makes a needle track.

8. The method of claim 7, wherein the collagenase is administered following the needle track.

9. The method of claim 2, wherein the concentration of the purified collagenase in the pharmaceutically acceptable liquid carrier is between 0.58 mg/ml and 1.16 mg/ml.

10. The method of claim 2, wherein the volume of the pharmaceutically acceptable liquid carrier is between 0.1 ml and 2.0 ml.

11. The method of claim 2, wherein the liquid pharmaceutically acceptable carrier is selected from the group consisting of normal saline, aqueous $NaCl/CaCl_2$ buffer, aqueous dextran solution, and aqueous hetastarch solution.

* * * * *